United States Patent
Pekander et al.

(10) Patent No.: US 10,588,529 B2
(45) Date of Patent: Mar. 17, 2020

(54) ECG MONITORING SYSTEM AND METHOD

(71) Applicant: General Electric Company, Schenectady, NY (US)

(72) Inventors: Otto Valtteri Pekander, Helsinki (FI); Emma Elina Ikonen, Helsinki (FI); Jussi Olavi Halinen, Helsinki (FI); Ville Petteri Vartiovaara, Helsinki (FI); Juha Petri Virtanen, Helsinki (FI)

(73) Assignee: General Electric Company, Schenectady, NY (US)

( * ) Notice: Subject to any disclaimer, the term of this patent is extended or adjusted under 35 U.S.C. 154(b) by 602 days.

(21) Appl. No.: 15/205,389

(22) Filed: Jul. 8, 2016

(65) Prior Publication Data

US 2018/0008158 A1 Jan. 11, 2018

(51) Int. Cl.
*A61B 5/04* (2006.01)
*A61B 5/0408* (2006.01)
*A61B 5/00* (2006.01)

(52) U.S. Cl.
CPC .......... *A61B 5/0408* (2013.01); *A61B 5/0006* (2013.01); *A61B 5/6801* (2013.01); *A61B 5/684* (2013.01)

(58) Field of Classification Search
CPC .............. A61B 5/04085; A61B 5/0006; A61B 5/04087; A61B 5/6833; A61B 2560/0412;
(Continued)

(56) References Cited

U.S. PATENT DOCUMENTS 6,496,705 B1 * 12/2002 Ng ................ A61B 5/0006
455/456.1
6,749,566 B2 6/2004 Russ
(Continued)

FOREIGN PATENT DOCUMENTS

EP 1359842 B1 5/2009
EP 2559280 A1 2/2013
(Continued)

OTHER PUBLICATIONS

Pending U.S. Appl. No. 14/586,393, filed Dec. 30, 2014, "Common Display Unit for a Plurality of Cableless Medical Sensors", MUURANTO.
(Continued)

*Primary Examiner* — Joseph A Stoklosa
*Assistant Examiner* — Brian M Antiskay
(74) *Attorney, Agent, or Firm* — Andrus Intellectual Property Law, LLP

(57) ABSTRACT

An ECG monitoring system includes two or more active electrodes, each active electrode having an electrode pad fixable to a patient to sense physiological potentials from the patient, a common connection port, and a wireless transmitter. The system further includes a common connector electrically connected to the common connector port of each of the two or more active electrodes to provide a comparator signal to each of the active electrodes. Each of the active electrodes compares the physiological potentials sensed at the electrode pad against the comparator signal to generate a cardiac signal, and then wirelessly transmits the cardiac signal with the wireless transmitter.

18 Claims, 7 Drawing Sheets

(58) Field of Classification Search
CPC ... A61B 5/0205; A61B 5/0402; A61B 5/0416; A61B 5/04012; A61B 5/1116; A61B 5/02405; A61B 5/04011; A61B 5/0456; A61B 5/0472; A61N 1/0492; A61N 1/0476; A61N 1/0484
USPC ............... 600/372, 382, 384, 386, 388–393, 600/508–509
See application file for complete search history.

(56) References Cited

U.S. PATENT DOCUMENTS

| | | | |
|---|---|---|---|
| 7,390,299 B2 | 6/2008 | Weiner et al. | |
| 8,475,368 B2 | 7/2013 | Tran et al. | |
| 2004/0173003 A1 | 9/2004 | Ibane | |
| 2005/0107716 A1* | 5/2005 | Eaton | A61B 5/0073 600/544 |
| 2006/0136768 A1 | 6/2006 | Liu et al. | |
| 2006/0284621 A1 | 12/2006 | Doi | |
| 2008/0171311 A1* | 7/2008 | Centen | G09B 23/288 434/265 |
| 2008/0284599 A1 | 11/2008 | Zdeblick | |
| 2009/0306485 A1* | 12/2009 | Bell | A61B 5/04085 600/301 |
| 2009/0318818 A1 | 12/2009 | Whitaker et al. | |
| 2010/0069735 A1* | 3/2010 | Berkner | A61B 5/04028 600/382 |
| 2010/0081950 A1* | 4/2010 | Reinstadtler | A61B 5/0408 600/509 |
| 2010/0168605 A1 | 7/2010 | Aarts | |
| 2011/0066051 A1 | 3/2011 | Moon | |
| 2011/0145894 A1 | 6/2011 | Morchon et al. | |
| 2012/0068855 A1 | 3/2012 | Matsumura | |
| 2012/0108917 A1 | 5/2012 | Libbus et al. | |
| 2013/0053674 A1 | 2/2013 | Volker | |
| 2013/0079618 A1* | 3/2013 | Sandmore | A61B 5/0478 600/393 |
| 2013/0109927 A1 | 5/2013 | Menzel | |
| 2013/0303871 A1* | 11/2013 | Brest Van Kempen | A61B 5/04004 600/372 |
| 2013/0337842 A1 | 12/2013 | Wang et al. | |
| 2014/0187883 A1 | 7/2014 | Lisogurski | |
| 2014/0275823 A1* | 9/2014 | Lane | A61B 5/04087 600/301 |
| 2015/0116130 A1 | 4/2015 | Grubis | |
| 2015/0257647 A1* | 9/2015 | Buck | A61B 5/0028 600/388 |
| 2017/0000369 A1* | 1/2017 | Hyde | A61B 5/04085 |

FOREIGN PATENT DOCUMENTS

| | | |
|---|---|---|
| EP | 1881784 B1 | 10/2013 |
| WO | 2014027273 A1 | 2/2014 |

OTHER PUBLICATIONS

Radius-7 brochure, Masimo, admitted prior art.
IntelliVue Cableless Measurement brochure, Philips, Jun. 2013.

* cited by examiner

ECG MONITORING SYSTEM AND METHOD

BACKGROUND

This disclosure generally relates to medical monitoring systems and devices, and more specifically to a method and system for ECG monitoring.

Electrocardiograms (ECGs) are graphic depictions of electrical activity in the heart. ECGs are produced by electrocardiographs which are available as stand alone devices, portable devices, and/or as integrated functions in various types of multi-vital sign monitoring devices. Typically, ECGs are used as diagnostic tools in various settings, such as hospitals and doctor's offices. ECGs comprise ECG waveforms for each of various leads, which are calculated based on cardiac signals recorded from electrodes attached to the patient. Various ECG recording methods are widely employed using various electrode configurations. To provide just a few examples, 3-lead ECG employing a three electrode arrangement, 5-lead ECG employing a five electrode arrangement, and a 12-lead ECG employing a ten electrode arrangement are all well known in the relevant field, along with other known electrode arrangements. Color coding standards for particular electrode locations are employed so that the electrodes can be visually differentiated, such as the color coding standard developed by the American Heart Association (AHA) and the color coding standard developed by the International Electrotechnical Commission (IEC).

ECGs are depicted by time (ms) versus voltage (μV) and typically are represented as a waveform. The typical five important aspects, or portions, of an ECG waveform are the P wave, QRS complex (represented as the combination of the Q, R, and S waves respectively), and T wave. The less frequently seen sixth portion is a U wave. The data produced from the graphical depictions are useful in diagnosis of patients to determine what, if any, and the extent to which heart-related problems exist in a patient. For instance, ECGs are used in diagnosing: cardiac arrhythmias (irregular heart rhythms), myocardial infarction (heart attacks), hyper- and hypokalemia (high or low potassium levels, respectively), blockage, ischemia (loss of oxygen due to lack of blood flow possibly from blockage), just to name a few, and may also assist in diagnosis of non-heart related ailments. Accordingly, ECGs are known and proven to be valuable tools in diagnosis heart and even non-heart-related problems with patients.

Particularly, the ECG waveforms are useful in determining whether certain conditions exist or the predisposition of such conditions occurring based on established patterns. Particularly, important information can be derived by measuring the time between certain waveforms; commonly reviewed time intervals are those between the P wave and the beginning of the QRS interval (known as the PR interval) and the time between the QRS complex and the T wave (known as the QT interval). Other relevant data may be derived from the PR segment, the QRS complex, and the ST segment.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, an ECG monitoring system includes two or more active electrodes, each active electrode having an electrode pad fixable to a patient to sense physiological potentials from the patient, a common connection port, and a wireless transmitter. The system further includes a common connector electrically connected to the common connector port of each of the two or more active electrodes to provide a comparator signal to each of the active electrodes. Each of the active electrodes compares the physiological potentials sensed at the electrode pad against the comparator signal to generate a cardiac signal, and then wirelessly transmits the cardiac signal with the wireless transmitter.

One embodiment of a method of ECG monitoring includes providing two or more active electrodes to be placed on a patient, each active electrode having an electrode pad to sense physiological signals from the patient, a common connection port, and a wireless transmitter. The method further includes providing a common connector that connects to the common connector port of each of the two or more active electrodes to create a comparator signal to each of the active electrodes. In each of the active electrodes, the method further includes generating a cardiac signal based on the physiological potentials sensed at the electrode pad and the common connection port, and wirelessly transmitting the cardiac signal with the wireless transmitter. The cardiac signal is received from each of the two or more active electrodes, and ECG waveforms are generated based on the cardiac signals.

One embodiment of a method of identifying electrodes with an ECG monitoring system includes receiving a cardiac signal from each of two or more electrodes placed on a patient according to an electrode configuration and generating ECG waveforms based on the two or more cardiac signals. The ECG waveforms are then compared to a signal pattern for each expected lead in the electrode configuration, and identifying a placement location for each of the two or more electrodes that is more probable based on the comparison. The respective placement location is then indicated on each electrode.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
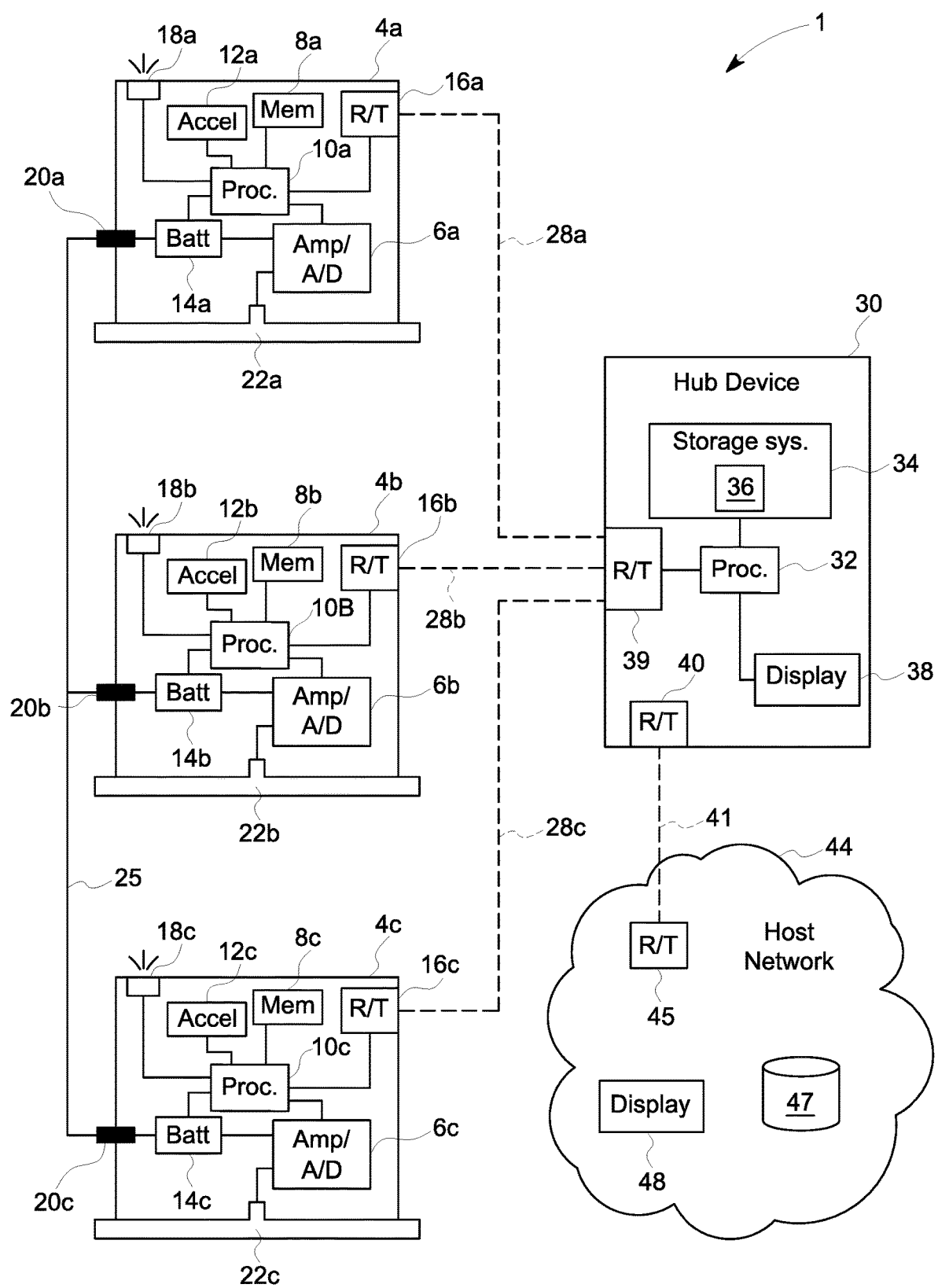
FIG. 1 depicts one embodiment of an ECG monitoring system according to the present disclosure.

Currently available ECG monitoring systems and methods typically require a wired connection between the electrodes connected to the patient and a monitor that receives the potentials measured by the electrodes and calculates ECG waveforms therefrom. Such systems often inhibit patient movement requiring a patient to stay in one location or to carefully transport a large monitor with them when they move from one place to another. Accordingly, the present inventors have recognized a need for a wireless ECG monitoring system that does not require a wired connection between the electrodes and a patient monitor, thereby allowing a patient to move more freely without concern of catching a wire and interrupting ECG monitoring by pulling off an electrode. However, the present inventors have also recognized that a major challenge to developing such a wireless ECG system is providing a common reference point for the measurement from each of the various wireless ECG electrodes. Accordingly, heretofore, effective wireless ECG systems utilizing a wireless connection between the electrodes and the ECG monitor have not been successfully developed.

The present inventors have also recognized that another problem with currently available ECG monitoring systems is that designated ECG electrodes must be used and placed correctly in the designated location so that the ECG monitoring system can correctly locate each ECG electrode and correctly calculate ECG waveforms therefrom. The use of designated ECG electrodes for each location is burdensome because it requires a clinician to have a proper set of three, five, ten, or more electrodes on hand, and to properly place each of these electrodes in the right location without inadvertently swapping or placing any of the electrodes at the wrong location. Further, should any of the electrodes break or otherwise pose a problem, an electrode of that same type must be used, thus requiring a clinician to have backups of each designated electrode type on hand.

A further problem recognized by the present inventors is that ECG electrode systems and devices often have a one-size-fits-all configuration, where a single electrode system or device is used for patients of all sizes. Such systems are often way too big and cumbersome for small patients, such as children, with excess wires hanging between electrodes that pickup unnecessary noise and cause unnecessary hazards of entanglement and inadvertently pulling off an electrode. On the other end of the spectrum, such single-sized electrode systems and devices often cannot fit on or accommodate very large patients and do not allow for proper electrode placement on such patients. Certain ECG electrode providers have solved this problem by manufacturing various sized electrode systems and electrode configurations, such as different systems for infants, children, adults, large adults, etc. Such a solution is not ideal because it requires facilities and clinicians to have multiple electrode configurations on hand, which is expensive, burdensome, and wasteful.

In recognition of the aforementioned problems and challenges posed by currently available ECG monitoring systems and methods, the present inventors developed the disclosed ECG monitoring system 1 which provides a single active electrode device 4 that wirelessly connects to a hub device 30. Multiple active electrodes 4 are utilized in a single ECG monitoring system 1 and wirelessly communicate via respective wireless receiver/transmitters 16 with the hub device 30, which may be by any of various available wireless communication protocols. The ECG monitoring system 1 can be variously sized to fit any patient. All of the active electrodes 4 in the system 1 utilized for a particular patient are connected by a common connector 25, which provides a comparator signal against which the physiological potentials measured by each electrode can be compared. Thus, the cardiac signals generated by each active electrode 4 have a common reference, allowing them to be compared to one another to generate the ECG waveforms. As described in more detail herein, the common connector 25 may be any device providing a common electrical connection between all of the active electrodes 4, such as a wire that is connected to all of the active electrodes 4 once the active electrodes are placed on the patient.

The ECG monitoring system 1 is depicted and exemplified herein as incorporating three active electrode devices 4 (i.e., 4a-4c); however, a person having ordinary skill in the art will understand in light of this disclosure that the system can incorporate any number of two or more active electrodes. All of the active electrodes 4 in the system 1 are wirelessly linked to a hub device 30 that receives the cardiac signals generated by each respective active electrode 4. In a preferred embodiment, each active electrode 4 in the ECG monitoring system 1 is configured identically. Thus a clinician setting up the system 1 only needs to be equipped with one type of sensor device and does not need to carry multiple different electrode configurations or sort out which electrodes go on which physical location on the patient. Instead, the clinician simply attaches an active electrode 4 at each placement location according to a known electrode configuration, and the ECG monitoring system automatically determines where each respective active electrode is on the patient 2, and in some embodiments may communicate the respective assignment to the clinician for verification. Thus, any number of active electrodes 4 (e.g., 3, 5, 410 active electrodes) can be positioned on the patient 2 according to any known electrode configuration standard utilized for ECG monitoring, and the ECG monitoring system 1 will automatically compare the respective cardiac signals generated by the various active electrodes 4 to generate appropriate ECG waveforms. Accordingly, the presently disclosed ECG monitoring system is versatile and expandable, such that the same system utilizing the single type of active electrode device can be utilized to perform any type of ECG monitoring.

FIG. 1 depicts an exemplary embodiment of an ECG monitoring system 1 having three active electrodes 4a-4c. Each active electrode 4a-4c is connected to common connector 25. More specifically, the common connector 25 is electrically connected to the common connection port 20a-20c of each of the active electrodes 4a-4c, respectively. Thereby, the common connector 25 provides comparator signal, a common signal to each of the active electrodes 4a-4c against which the physiological potentials sensed by the electrode pad 22a-22c can be compared. In the depicted example, the common connector 25 is connected to each of the batteries 14a-14c, creating a battery ground used as the input to the amplification and analog-to-digital conversion module 6a-6c of each active electrode 4a-4c.

Each active electrode 4a-4c communicates with hub device 30 via a respective wireless communication link 28a-28c, which may be by any of a multitude of various available wireless communication protocols. Specifically, each active electrode 4a-4c has a wireless receiver/transmitter 16a-16c that communicates with a receiving device, such as receiver/transmitter 39 of the hub device 30 and/or a receiver/transmitter 45 in a host network 44. Thereby, the hub device 30 and/or host network 44 receives the cardiac signal recorded and generated by each active electrode 4a-4c and can compares the cardiac signals to generate ECG waveforms. In an embodiment including the hub device 30, the hub device 30 may display the ECG waveforms on a display 38 integrated into or otherwise associated with the hub device 30, and then transmit the ECG waveforms to host network 44 for storage in database 47, such as a patient medical record database or an ECG database (e.g., a MUSE ECG management system available by General Electric Company of Schenectady, N.Y.).

In the depicted embodiment, the hub device 30 communicates wirelessly with the host network 44 via wireless communication link 41 between receiver/transmitter 40 in the hub device 30 and receiver/transmitter 45 associated with the host network 44. The host network 44 may be, for example, a local computer network for a medical facility, such as a hospital, including servers housed therein. In other embodiments, the host network 44 may include a cloud-based system housed by a cloud computing provider. The host network 44 may include user interface devices through which clinicians may interface with the ECG monitoring system 1, such as to see the ECG waveforms produced therefrom and/or any alerts or other notices outputted by the ECG monitoring system 1. For example, the user interface of the host network 44 may include a display 48, such as a central patient monitoring display commonly provided at nursing stations or other patient care stations in a medical facility.

In various embodiments, the hub device 30 may be a portable device placed on or near a patient wearing the active electrodes 4a-4c. In certain embodiments, the hub device 30 may be a stand-alone device placed in proximity of the patient 2 during ECG monitoring. In other embodiments, the hub device 30 may be incorporated into a multi-function patient monitor that monitors multiple physiological aspects of the patient. In still other embodiments, the hub device 30 may take the form of a multipurpose computer or consumer electronic device, such as a smart phone or tablet computer, having on or more software applications executable to perform the steps and function described herein.

In one embodiment, the active electrodes 4a-4c and hub device 30, via respective receiver/transmitter's 16a-16c and 39, may be configured as medical body area network (MBAN) devices and communicate according to MBAN-related wireless protocols. In other embodiments, the receiver/transmitters 16a-16c and 39 may communicate via other relatively short-range radio protocols, such as Bluetooth Low Energy (BLE), ANT, ZigBee, or near field communication (NFC). In other embodiments, the commination may be via network protocols appropriate for longer range wireless transmissions, such as on the wireless medical telemetry service (WMTS) spectrum or on a Wi-Fi-compliant wireless local area network (WLAN). Likewise, the receiver/transmitter 40 in the hub device 30 may communicate with the receiver/transmitter 45 in the host network by any such wireless communication protocol, and in certain common embodiments the longer-range wireless transmission protocols, such as WMTS and WLAN, may be preferred. In still other embodiments, the respective receiver/transmitters 16a-16c, 39, 40 and 45 may be capable of switching between two or more wireless communication protocols, such as to optimize data communication based on the situation.

In still other embodiments, the hub device 30 may be eliminated and each of the active electrode 4a-4c may communicate directly with the host network 44. In such an embodiment, the respective wireless communication links 28a-28c would be with the receiver/transmitter 45 of the host network 44, and could be accomplished via any of various network protocols appropriate for longer-range wireless transmissions, such as on the WMTS spectrum or on a WLAN, as described above.

Each active electrode 4a-4c has an electrode pad 22a-22c that connects to the patient's skin to record physiological potentials from the patient's body. The electrode pads 22a-22c may take any form that provides a sufficient electrical connection to the patient's skin, such as reusable or disposable electrode pads. For example, the electrode pads 22a-22c may be adhesive snap electrode pads, such as adhesive foam electrode pads produced by, for example, 3M Company of Maplewood, Minnesota. The electrode pad 22a-22c may be removable from the active electrode 4a-4c, such as in an embodiment where the active electrode 4a-4c is reusable and configured to accept or connect to a disposable electrode pad 22a-22c. In other embodiments, the electrode pad 22a-22c is permanently fixed and/or integrated into the active electrode 4a-4c, and is not removable or replaceable. In such an embodiment, the entire active electrode 4a-4c may be configured as a disposable electrode intended to be a single-use device. Alternatively, the active electrode 4a-4c may be reusable and configured to be cleanable.

Each active electrode 4a-4c contains a battery 14a-14c to power the various components therein. The batteries 14a-14c may be rechargeable batteries or disposable batteries. In certain embodiments, the batteries 14a-14c may be removable and replaceable from the active electrode device 4a-4c, or may be an integral component of the active electrode 4a-4c that is not removable or replaceable. In such embodiments, the entire active electrode 4a-4c may be configured to connect to a charging device to charge the battery 14a-14c, such as inserted into a charging station configured to charge multiple active electrodes 4a-4c. In such an embodiment, the system 1 may be configured such that the respective electrode pad 22a-22c can remain on the patient and a new active electrode 4a-4c may be connected to the respective electrode pad 22a-22c when the battery 14a-14c runs low and needs to be recharged.

Each active electrode senses physiological potentials from the patient through the electrode pad 22a-22c and generates a cardiac signal based on the sensed physiological potentials. As described above, each active electrode 4a-4c has a common connection port 20a-20c through which the electrode receives the comparator signal from the common connector 25. As each of the active electrodes 4a-4c is connected to the same common connector 25, each of the active electrodes 4a-4c receives the same comparator signal. The common connector 25 is generally a passive electrical connection between each of the active electrodes 4a-4c which can be generally said to provide an average of the ambient electrical activity seen by the active electrodes 4a-4c. In the depicted embodiment, the common connector 25 connects to each of the batteries 14a-14c in the active electrodes 4a-4c, thereby also acting as a battery ground and accounting for electrical noise in the comparator signal, and thus allowing for removal of such base line noise.

The common connector 25 may be comprised of any conductive material that is sufficiently pliable in order to be connected between the various active electrodes 4 (e.g., 4a-4c), which may be applied to a patient in any of various configurations and applied to all patients ranging in size from a tiny infant to a very large adult. In certain embodiments it is preferable that the conductor of the common connector 25 be insulated. For example, the common conductor may be a soft, flexible substrate, such as a thermoplastic polyurethane (TPU) or rubber-like material, with a conductive trace, or wire, printed thereon. For example, the conductive wire may be printed on the flexible substrate with a conductive ink, such as a powdered or flaked silver material or a carbon-like material. A second layer of flexible substrate may be placed over the printed wire in order to complete the insulation surrounding the wire. In one embodiment, the material for the common connector 25 may be supplied in a bulk format, such as on a reel or other dispenser, so that the clinician setting up the ECG monitoring system 1 can dispense a proper amount of the common connector 25 necessary to connect between the various active electrodes 4a-4c. For example, a section of the common connector 25 material of the appropriate size may be cut from the bulk supply and attached to each of the active electrodes 4a-4c, and specifically to the common connection port 20a-20c of each active electrode 4a-4c. In one embodiment, the common connection port 20a-20c may include a pin or some sort of protrusion made from a conductive material capable of punching through the insulation of the common connector 25 in order to provide an electrical connection with the conductive material in the common connector 25. In one embodiment, each active electrode 4a-4c has a clip or snapping mechanism that places pressure at a connection point at the common connector 25 in order to force a connection between the common connector 25 and the common connection port 20a-20c and to hold the common connector in place against the common connection port 20a-20c.

Each active electrode 4a-4c has a signal processing module 6a-6c that amplifies and digitizes the physiological potentials sensed through the respective electrode pads 22a-22c to generate a respective cardiac signal. The signal processing module 6a-6c may include amplification circuitry that compares the physiological potentials sensed at the respective electrode pad 22a-22c to the comparator signal, such as a differential amplifier or a comparator circuit. The signal processing module 6a-6c further includes an analog-to-digital (A/D) converter to convert the amplified analog signal to a digital cardiac signal. The A/D converter may be any device or logic set capable of digitizing analogs physiological signals at an appropriate sampling rate. For example, the A/D converter may be an analog front end (AFE). The signal processing module 6a-6c may further include other circuitry and/or software for amplifying, filtering, or otherwise conditioning the cardiac signal before transmission to the hub device 30 and/or host network 44. Alternatively or additionally, software for filtering and signal conditioning may be stored in memory 8a-8c and executed by the respective processor 10a-10c within the active electrode 4a-4c.

In one embodiment, the sampling by the A/D converters in each of the active electrodes 4a-4c is coordinated so that the cardiac signal from each respective active electrode 4a-4c can be aligned and compared by the hub device 30. In one embodiment, the hub device 30 generates a timing beacon, which is a timing signal universally wirelessly transmitted to all of the active electrodes 4a-4c connected thereto. For example, the timing beacon may be transmitted to each active electrode 4a-4c via the respective communication link 28a-28c between the receiver/transmitter 39 in the hub device 30 and the receiver/transmitter 16a-16c in each active electrode 4a-4c. The timing beacon is utilized by the A/D converter to time the sampling of the analog signal, such as utilized as a timing instruction, so that the sampling at all active electrodes 4a-4c is coordinated. Alternatively or additionally, the active electrode 4a-4c may adjust its internal clock to coordinate with the timing beacon, such as the clock of the respective processor 10a-10c. Additionally, each active electrode 4a-4c can send its own oscillator value upon detecting the timing beacon. Then each sample or data package has a current oscillator value included so that the hub device 30 can calculate the time that the sample was taken. In other words, the sampling frequency at each active electrode 4a-4c can be calculated from the oscillator values, and the samples from the various active electrodes 4a-4c can be aligned using the oscillator values within the data.

Each active electrode 4a-4c includes a processor 10a-10c that executes computer readable instructions stored in memory 8a-8c to control the various components in the active electrode 4a-4c to preform as described here in. The processor 10a-10c may further provide power control functions between the battery 14a-14c and other components, and may further facilitate communication between components.

In certain embodiments, each active electrode 4a-4c may include an accelerometer 12a-12c configured to sense motion of the active electrode 4a-4c. For example, as described further, information from the respective accelerometer 12a-12c may be utilized by the processor 10a-10c to determine when an active electrode 4a-4c is removed from its charging location, and such input may be the basis for determining when to turn on, or activate, the various components of the active electrode 4a. Alternatively or additionally, input from the accelerometer 12a-12c may be utilized to sense when the active electrode 4a-4c is tapped by a user or clinician, which as described here in can be one way of receiving user input for activating (or turning on) the active electrode or determining and assigning the correct electrode position on the patient 2.

In various embodiments, each active electrode 4a-4c may further include one or more LEDs 18a-18c, which may be used to indicate various information to the clinician. For example, the processor 10a-10c may illuminate an LED 18a-18c when the respective active electrode 4a-4c is on (e.g., the battery is powering certain components of the device), or to indicate when the respective receiver/transmitter 16a-16c is operating an active communication link 28a-28c with the hub device 30. Alternatively or additionally, the LEDs 18a-18c may be utilized to indicate a charged status of the respective of the battery 14a-14c, such as by illuminating or flashing the respective LED 18a-18c when the battery charge status is low. In other embodiments, the LEDs 18a-18c may be utilized as a location indicator to indicate an assigned electrode placement location for that active electrode 4a-4c. In such an embodiment, the LEDs 18a-18c may be multicolored LEDs, which are controlled to illuminate in a particular color once the electrode locations have been determined by the hub device 30. More specifically, the multicolored LEDs 18a-18c may each be configured to illuminate in any of various colors to indicate the placement location assigned to that particular active electrode 4a-4c. For example, each of the LEDs 18a-18c may be able to illuminate in any of the colors according to an appropriate color coding standard such as the AHA or IEC color coding standards and thus may illuminate in the color corresponding to its assigned electrode location according to that particular color coding standard. Thereby, a clinician can tell if the system 1 has correctly assigned the electrode locations by just looking at the electrodes illuminated on the patient. Each active electrode 4a-4c may have multiple LEDs for serving the various aforementioned purposes, or may variously control a single LED 18a-18c on each active electrode 4a-4c to provide one or more of the aforementioned functions.

Figure 2:
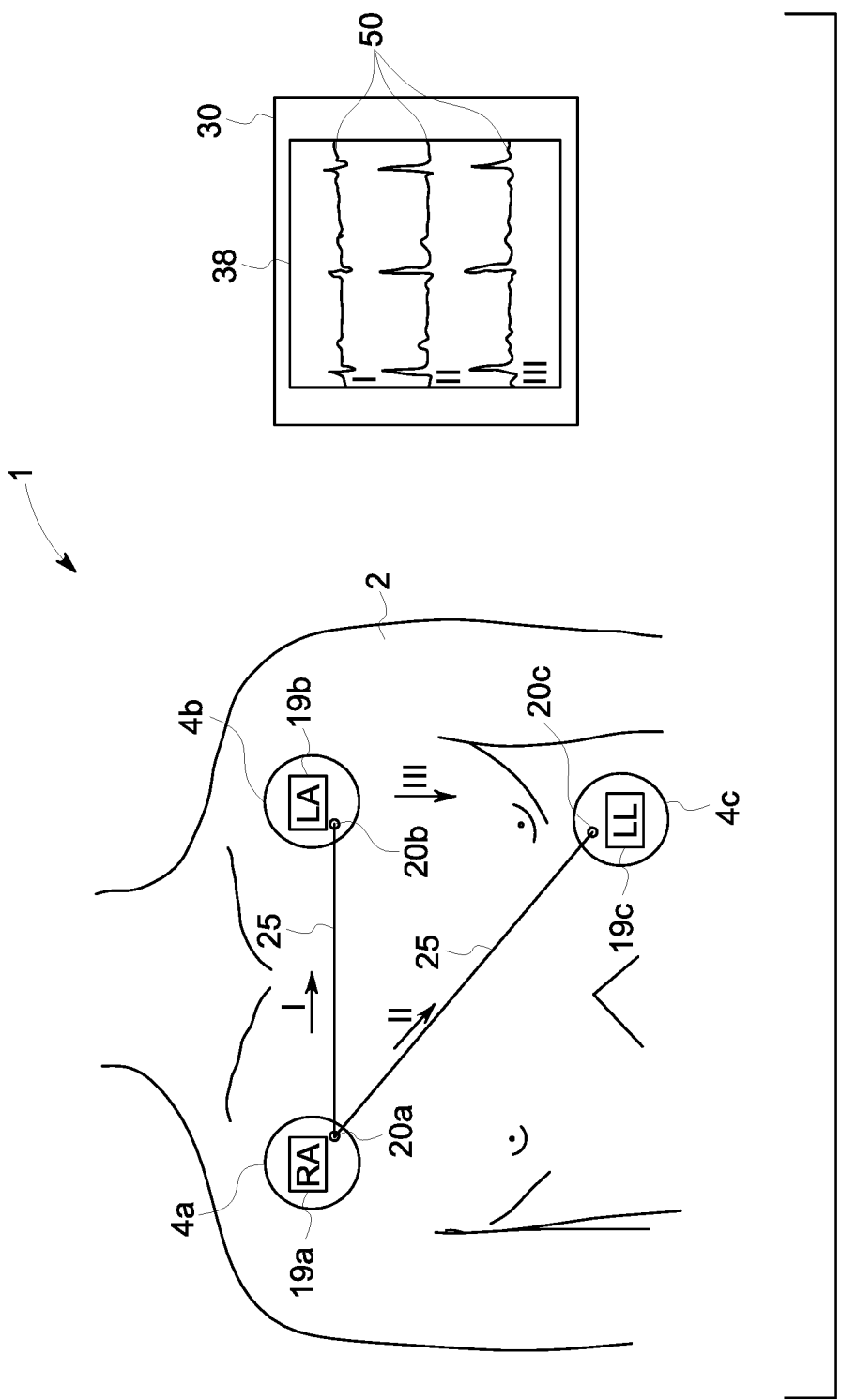
FIG. 2 depicts another embodiment of the CCG monitoring system according to the present disclosure.

In other embodiments, the active electrodes 4a-4c may include a display that can be controlled to display information about the status of the active electrode 4a-4c, such as power or connectivity status, battery charge status, and or as location indicators to display the assigned placement location of the respective active electrode 4a-4c. FIG. 2 depicts one embodiment of an ECG monitoring system 1 including three active electrodes 4a-4c placed on a patient 2 at predefined placement locations forming a common three lead ECG arrangement. Each active electrode 4a-4c has an adjustable display 19a-19c performing as a location indicator to display its assigned placement location. Specifically, active electrode 4a has display 19a displaying "RA", representing the right arm placement location. Active electrode 4b has display 19b displaying "LA" representing the left arm placement location of that active electrode. Active electrode 4c has display 19c displaying "LL" representing the left leg placement location for that electrode. The displays 19a-19c may be any of various known small electronically-controlled display device, such as an LED display, an LCD display, and electronic paper display, and electroluminescent display, or the like.

The electrodes 4a-4c are connected by common connector 25 connected to the common connector port 20a-20c of each of the active electrodes 4a-4c. Each of the active electrodes generates and wirelessly transmits a cardiac signal to the hub device 30 as is described above. The hub device 30 then generates appropriate ECG waveforms 50 based on the configuration of active electrodes 4a-4c on the patient 2. Referring to the electrode configuration depicted in FIG. 2, the hub device 30 generates a three lead ECG—lead I generated based on the cardiac signals from active electrode 4a and 4b, lead II generated based on cardiac signals from active electrodes 4a and 4c, and lead III generated based on cardiac signals received from active electrodes 4b and 4c. The hub device 30 may include a display 38 that displays the ECG waveforms 50. Additionally, the display 38 may provide a user interface function for the ECG monitoring system 1, such as to display instructions to the clinician regarding the status of the system or any of the active electrodes 4a-4c in the system. Alternatively or additionally, the display 38 on the hub device 30 may be a touch screen allowing the clinician to provide control inputs to the ECG monitoring system 1.

In certain embodiments, the hub device 30 has an electrode identification module 36, which is a software module comprised of computer executable instructions stored in memory, such as in storage system 34 of the hub device 30. The electrode identification model 36 is executable by the processor 32 to determine a placement location for each active electrode 4a-4c in the system 1. The electrode identification module 36 may be configured to make that determination based on the cardiac signal wirelessly transmitted from each active electrode 4a-4c. For example, the electrode identification module 36 may be configured to compare the various cardiac signals received from the active electrodes 4a-4c to one another in order to generate waveforms. The generated waveforms are then compared to expected pattern for each expected lead based on, for example, the number of electrodes transmitting cardiac signals and/or input from the clinician regarding the electrode configuration being employed. For example, the electrode identification module 36 may generate waveforms for all potential electrode combinations based on the cardiac signals received at the hub device 30, and may compare those waveforms to an expected pattern for each lead to determine which of the waveforms most closely conform to the expected pattern. Alternatively, the electrode identification module 36 may be configured to start by generating a subset of the possible potential waveforms and making further analysis and determination based on the initial subset.

Thereby, a placement location can be determined for each electrode based on the leads that are identified as involving the cardiac signal from that active electrode 4a-4c. With reference to the example of FIG. 2 for example, if the cardiac signal from a particular electrode is identified as being part of a waveform that matches lead I and a waveform that matches lead II, the placement location can be determined as the Right Arm RA location.

In another embodiment, the placement location may be determined based on user input, such as input from a clinician provided at the various active electrodes for 4a and 4c and/or via the user interface on the hub device 30. For example, the clinician may touch or tap each of the active electrodes 4a-4c in a predefined order, and each active electrode 4a-4c senses the tapping via its embedded accelerometer 12a-12c. For example, each active electrode 4a-4c may be configured to immediately transmit a notification to the hub device 30 upon sensing a topping, and the hub device 30 can then determine the electrode placement based on the order that the notifications are received and which active electrode 4a-4c transmitted such notifications. As will be understood by a person having ordinary skill in the art, the active electrodes 4a-4c and the hub device 30 may utilize identification numbers or codes includes in the wireless transmissions between the hub device 30 and each active electrode 4a-4c so that the hub device 30 can identify and track the various signals emanating from each active electrode 4a-4c.

For example, the hub device 30 may present instructions to a clinician, such as on the display 38, to tap the active electrodes 4a-4c in a particular order. Alternatively or additionally, the hub device 30 may instruct the clinician to confirm or input the electrode configuration of the active electrodes 4a-4c on the patient. For example, in one embodiment the hub device 30 may recognize the number of active electrodes 4a-4c transmitting cardiac signals, and may assume an electrode configuration based on that number. The hub device 30, such as executing instructions of the electrode identification module 36 can display the assumed electrode configuration on the display 38. The hub device 30 may the receive input from the clinician, such as through a touch screen embodiment of display 38, to accept or modify the assumed electrode configuration. The display 38 may then be controlled to instruct the clinician to tap, touch, or otherwise identify each of the active electrodes 4a-4c in a particular order so that the hub device 30 can determine which transmitting active electrodes 4a-4c are in which of the placement locations for the identified electrode configuration.

The exemplary system diagram of FIG. 1 is intended to show just one exemplary system, and a person having ordinary skill in the art will understand in light of this disclosure that many other configurations are possible. In the depicted embodiment, the active electrodes 4a-4c are communicatively connected to the hub device 30 and the electrode identification module 36 is stored and executed within the hub device 30 to perform the methods disclosed and described herein. In other embodiments, the electrode identification module 36 may be stored and executed within computing systems of the host network 44.

With exemplary reference to FIG. 1, the processing system of the hub device 30, which includes processor 32, loads and executes software from the storage system 34, including the electrode identification module 36, which is an application within the software. The hub device 30 may have a processing system comprised of processor 32 and other circuitry that retrieves and executes software from storage system 34. Exemplary processors include general purpose central processing units, applications specific processors, and logic devices, as well as any other type of processing device, combinations of processing devices, or variations thereof. Processing system can be implemented within a single processing device but can also be distributed across multiple processing devices or sub-systems that cooperate in executing program instructions. Electrode identification module 36 includes computer-readable instructions that, when executed direct the processing system to operate as described in herein in further detail, including to execute steps to identify the placement location of each active electrode 4 in the ECG monitoring system 1.

Although the example embodiment of FIG. 1 includes one electrode identification module 36 stored and executed entirely within the hub device 30, it should be understood that one or more software elements having one or more modules may provide the same operation, and that such software elements performing aspects of the disclosed method may be distributed across the various hardware elements of the system (including on the active electrodes 4, the hub device 30, and/or the host network 44).

The storage system 34, can comprise any storage media, or group of storage media, readable by processor 32 and capable of storing software. The storage system 34 can include volatile and non-volatile, removable and non-removable media implemented in any method or technology for storage of information, such as computer-readable instructions, data structures, program modules, or other data. Storage system 34 can be implemented as a single storage device but may also be implemented across multiple storage devices or sub-systems. Examples of storage media include random access memory, read only memory, magnetic discs, optical discs, flash memory, virtual memory, and non-virtual memory, magnetic sets, magnetic tape, magnetic disc storage or other magnetic storage devices, or any other medium which can be used to storage the desired information and that may be accessed by an instruction execution system, as well as any combination or variation thereof, or any other type of storage medium. Likewise, the storage media may be housed locally with the processing system 34, or may be distributed in one or more servers, which may be at multiple locations and networked, such as in cloud computing applications and systems. In some implementations, the storage media can be a non-transitory storage media. In some implementations, at least a portion of the storage media may be transitory.

Figure 3:
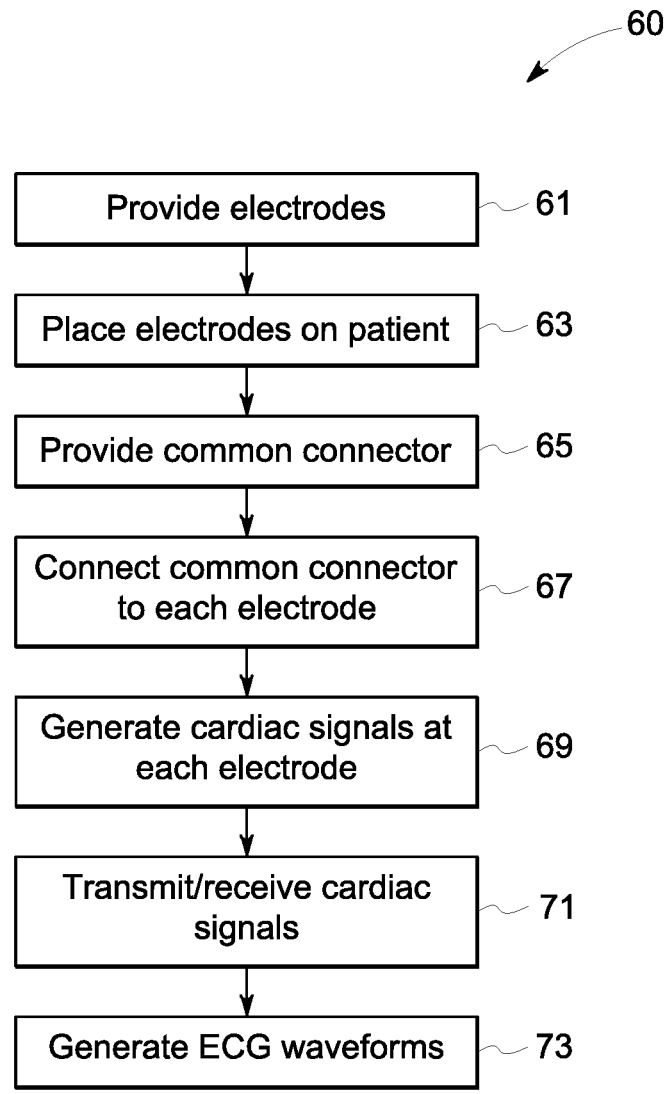
FIG. 3 depicts one embodiment of a method of monitoring ECG according to the present disclosure.

FIG. 3 depicts one embodiment of a method 60 of monitoring ECG. At step 61, electrodes are provided, such as the active electrode devices 4a-4c described herein. At step 63, the electrodes are placed on a patient, such as a clinician adhering the active electrodes 4a-4c to the skin of the patient. A common connector 25 is provided at step 65, such as a dispenser containing a bulk supply of the insulated conductor as described herein, and the common connector is connected to each electrode at step 67, such as an electrical connection made between the common connector and the common connection port 20a-20c of each active electrode 4a-4c. Cardiac signals are then generated at each electrode at step 69, such as by each active electrode 4a-4c based on the physiological potentials sensed at its electrode pad 22a-22c and the comparator signal. At step 71, the cardiac signals are transmitted by each electrode and received at a central device, such as a hub device 30 or host network 44.

The central device then generates ECG waveforms at step 73 based on the cardiac signals received from the electrodes.

Figure 4:
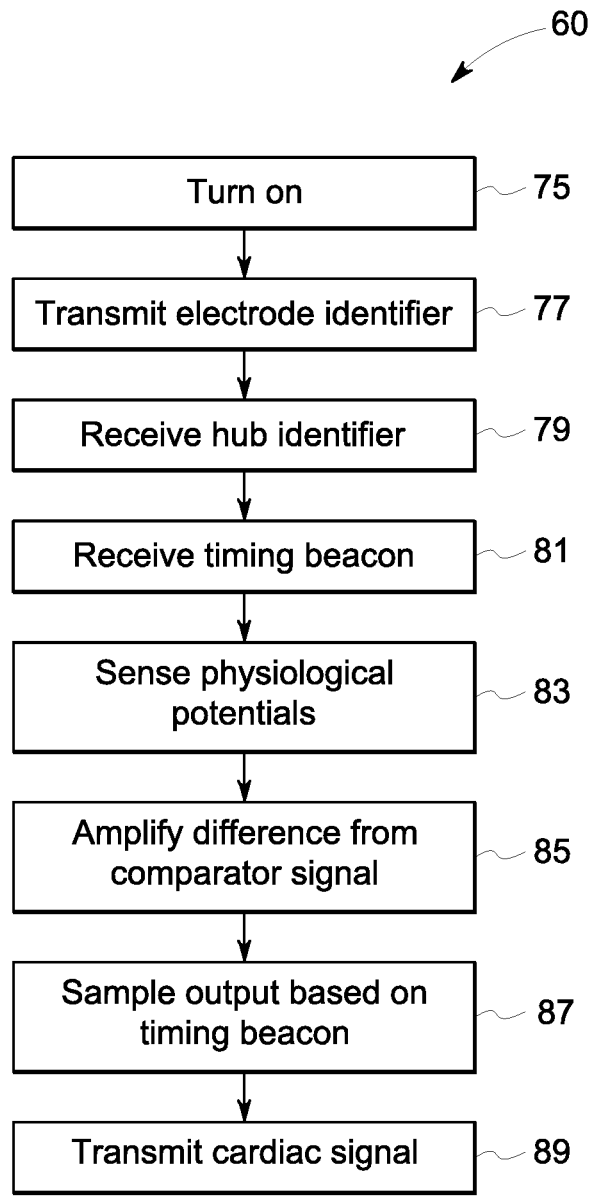
FIG. 4 depicts another embodiment of a method of monitoring ECG according to the present disclosure, and specifically a method portion executed within the electrode portion of the disclosed ECG monitoring system.

FIG. 4 depicts another embodiment of a method 60 of monitoring ECG, and specifically a method portion that may be executed within the active electrodes 4a-4c. For example, the depicted steps may be embodied in computer readable software code stored in memory 8a-8c within each active electrode 4a-4c, and may be executed by executing the software instructions on the respective processor 10a-10c in that active electrode 4a-4c. The active electrode 4a-4c turns on at step 75. As described herein, the active electrodes 4a-4c may automatically turn on based on some condition within the system, such as separation form a charging device or the sensing of emotion by the accelerometer 12a-12c therein. Alternatively, the active electrode 4a-4c may turn on based on a user input, such as a user pressing a power button on the active electrode 4a-4c. Once the active electrode is turned on, it may execute step 77 to transmit an electrode identifier, such as to the hub device 30 or host network 44. The active electrode may receive a hub identifier at step 79, such as from the hub device 30, which may be part of a pairing process between the active electrode 4a-4c and the hub device 30 or host network 44. The active electrode 4a-4c receives a timing beacon at step 81 from the hub device 30 or host network 44 which will provide a basis for the synchronization of sampling the physiological potentials recorded from the patient. The physiological potentials are sensed at step 83, such as through the electrode pad 22a-22c. The physiological potentials are the processed at step 85 to compare the physiological potentials to the comparator signal from the common connector 25 and to amplify a difference between the two signals. The amplified signal is then sampled at step 87 based on the timing beacon. The resulting digitized cardiac signal is then wirelessly transmitted at step 89, such as via the wireless communication links between the active electrodes 4a-4c and the hub device 30 and/or host network 44.

Figure 5A:
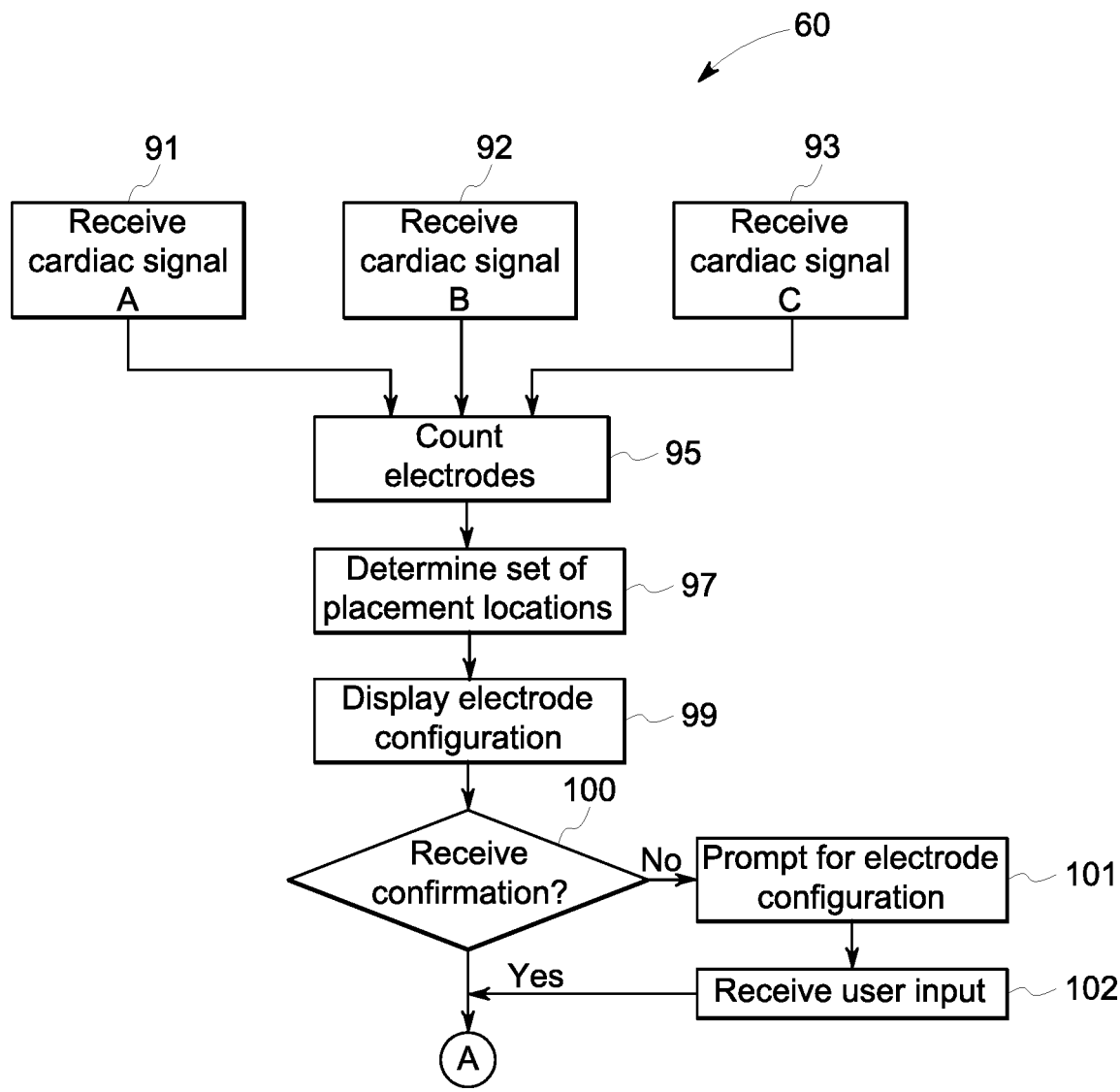
FIGS. 5A-5C depict other exemplary embodiments of methods of monitoring ECG according to the present disclosure, and specifically method portions executed within a hub device of the disclosed ECG monitoring system.
Figure 5B:
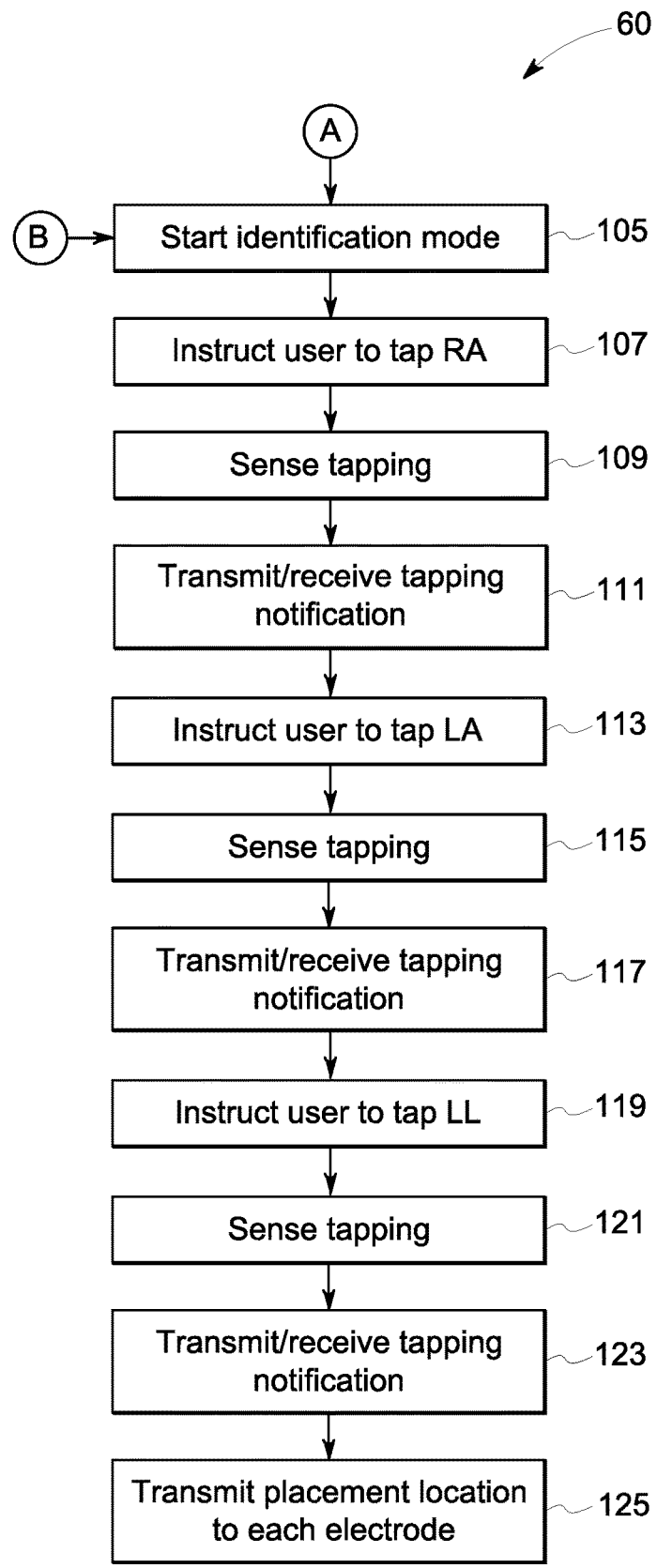
Figure 5C:
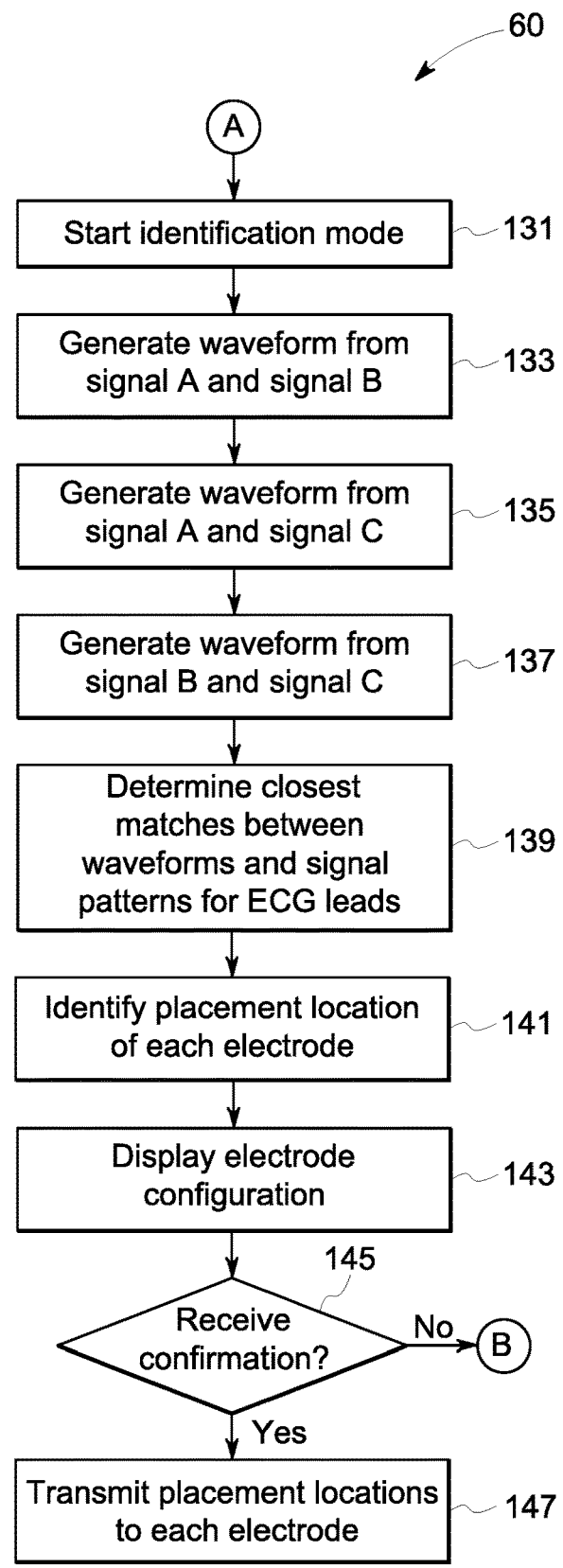

FIGS. 5A-5C depict other exemplary embodiments of methods 60 of monitoring ECG, and specifically methods portions that may be executed within a hub device 30 or host network 44 receiving the cardiac signals from the active electrodes 4a-4c. For example, FIGS. 5A-5C depict exemplary steps that may be carried out by executing the instructions of the electrode identification module 36. FIG. 5A depicts an exemplary set of initial steps executed to receive cardiac signals from the various active electrodes 4a-4c in the system 1 and to determine an electrode configuration and corresponding set of possible placement locations for the various active electrodes 4a-4c. Cardiac signals are received from each of the active electrodes 4a-4c at steps 91, 92, and 93. The number of active electrodes is counted at step 95 providing a basis for determining a set of potential placement locations, or electrode configurations, at step 97. For instance, in the depicted example where 3 cardiac signals are received, the set of placement locations may be determined to be the placement locations of the most common three electrode configuration of the right arm, left arm, and left leg electrodes (see FIG. 2). Alternatively or additionally, the set of placement locations may be established based on input from a clinician and/or based on intelligent assessment of the cardiac signals. For instance, instructions may be executed to select the most probable standard electrode configuration based on comparison of the received cardiac signals to signal patterns for various possible standard electrode configurations based on the number of active electrodes 4a-4c communicating cardiac signals.

At step 99 the electrode configuration corresponding to the set of placement locations determined at step 97 may be displayed to the clinician for confirmation, such as on the display 38 of the hub device 30. If confirmation is received at step 100 that the electrode configuration, and thus the set of potential placement locations, is correct, then the system continues on to execute instructions to identify which electrode is at which placement location. If confirmation is not received at step 100, then the clinician may be prompted at step 101 to input the correct electrode configuration so that the proper set of potential placement locations can be obtained. Corresponding user input is then received at step 102, such as from the user interface associated with the hub device 30 or host network 44.

FIG. 5B depicts one embodiment of a portion of method 60 of ECG monitoring including steps executed to determine the placement location of each active electrode 4a-4c. At step 105, the ECG monitoring system 1 goes into identification mode, such as by input from the user to the hub device 30 or by execution of instructions to automatically determine that all active electrodes 4a-4c in the system are transmitting proper cardiac signals (and thus a determination that all active electrodes 4a-4c are connected to the patient 2). The clinician is instructed at step 107 to tap the electrode at a first placement location, such as one of the potential placement locations determined by the steps depicted in 5A. For example, such instructions may be provided to the clinician on the display 38 of the hub device 30. In the exemplary embodiment, the clinician is instructed at step 107 to tap the electrode at the Right Arm RA location. The tapping is sensed by the electrode at the RA location at step 109, such as by the accelerometer 12a-12c in that respective electrode. That electrode transmits a tapping notification at step 111, which is received by the hub device 30 or host network 44 executing the instructions of the electrode identification module 36. Likewise, the clinician is instructed at step 113 to tap the Left Arm LA active electrode. The tapping is sensed at the active electrode 4a-4c at the LA location at step 115, and the tapping notification is transmitted and received at step 117. Likewise, the clinician is instructed to tap the electrode at the Left Leg LL placement location at step 119, the tapping is sensed at step 121 by the active electrode 4a-4c at the LL location, and is then transmitted and received at step 123. The placement location for each active electrode 4a-4c has thereby been identified and determined, and the placement location can then be transmitted to each electrode at step 125 and can also be stored at a memory location within the system 1 so that the ECG waveforms can be generated accordingly based on the received cardiac signals.

FIG. 5C depicts another embodiment of method steps that may be executed to determine the placement location of each electrode, such as steps executable by the electrode identification module 35 to automatically determine a placement location for each active electrode 4a-4c, which can then be verified or confirmed by a user. The identification mode is started at step 131, which may take any of various forms as described above. Instructions are executed to generate waveforms from various possible cardiac signal combinations (exemplified at steps 133-137) and the waveforms are then compared to expected signal patterns for each of the leads devised from the electrode configuration on the patient 2. For instance, at step 133 a waveform is generated from cardiac signal A and cardiac signal B received from two active electrodes on the patient. Likewise, a waveform is generated from cardiac signal A and cardiac signal C at step 135, and a waveform is likewise generated from cardiac signal B and cardiac signal C at step 137. Accordingly, in the depicted embodiment, all possible permutations of waveforms are generated from the cardiac signals received. At step 139, instructions are executed to determine the closes matches between the waveforms generated at steps 133-137 and expected signal patterns for each of the ECG waveforms in each lead. For example, the signal patterns may be morphological-based patterns, such as expected amplitude and/or time values of particular portions of the QRS waveforms. Once the waveforms are matched to the leads, the placement location of each electrode can be determined at step 141. The electrode configuration is then displayed at step 143, e.g., on the display 38 of the hub device 30. Confirmation that the electrode configuration is correct may be received at step 145, and the placement locations may then be transmitted to each electrode at step 147. If confirmation is not received at step 145, and instead a rejection is received from the user, for example, then the system may request input from the clinician to correct and/or identify the placement location of each electrode, such as by the method steps exemplified in FIG. 5B.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. An ECG monitoring system comprising:
   two or more active electrodes, each active electrode having:
      an electrode pad fixable to a patient to sense physiological potentials from the patient;
      a common connection port; and
      a wireless transmitter;
   a common connector electrically connected to the common connection port of each of the two or more active electrodes to provide a comparator signal to each of the active electrodes; and
   wherein each of the active electrodes includes a signal processing module configured to compare the physiological potentials sensed at the electrode pad against the comparator signal to generate a cardiac signal representing the physiological potentials for the active electrode, and wherein each active electrode is configured to wirelessly transmit the cardiac signal with the wireless transmitter.

2. The ECG monitoring system of claim 1, further comprising a hub device communicatively connected to the wireless transmitter of each of the two or more active electrodes, wherein the hub device receives the cardiac signal from each active electrode and generates one or more ECG waveforms based thereon.

3. The ECG monitoring system of claim 2, wherein the signal processing module of each active electrode is configured to amplify a difference between the physiological potentials sensed at the electrode pad and the comparator signal to generate the cardiac signal.

4. The ECG monitoring system of claim 3, wherein each active electrode includes an analog-to-digital converter that samples the amplified difference between the physiological potentials sensed by the electrode pad and the comparator signal to generate the cardiac signal;
wherein the hub device generates a timing beacon; and
wherein the two or more active electrodes receive the timing beacon and sample the amplified difference based on the timing beacon.

5. The ECG monitoring system of claim 2, wherein the hub device includes a processor and an electrode identification module executable on the processor to determine a placement location for each of the two or more active electrodes.

6. The ECG monitoring system of claim 5, wherein the electrode identification module determines the placement location based on the cardiac signal generated by each of the active electrodes and/or the ECG waveforms generated at the hub device.

7. The ECG monitoring system of claim 5, wherein the electrode identification module determines the placement location based on user input.

8. The ECG monitoring system of claim 7, wherein each active electrode further includes an accelerometer that senses a motion of the active electrode, wherein the user input includes a user tapping each of the two or more active electrodes in a predefined order, and wherein the accelerometer senses the tapping.

9. The ECG monitoring system of claim 5, wherein the hub device communicates the placement location for each active electrode to that active electrode, and wherein each active electrode includes a location indicator that indicates the placement location for that active electrode.

10. A method of ECG monitoring, the method comprising:
providing two or more active electrodes to be placed on a patient, each active electrode having an electrode pad to sense physiological signals from the patient, a common connection port, a signal processing module, and a wireless transmitter;
providing a common connector that connects to the common connector port of each of the two or more active electrodes to create a comparator signal to each of the active electrodes;
in each of the active electrodes,
generating, with the signal processing module, a cardiac signal based on the physiological potentials sensed at the electrode pad and the comparator signal;
wirelessly transmitting the cardiac signal with the wireless transmitter;
receiving the cardiac signal from each of the two or more active electrodes; and
generating one or more ECG waveforms based on the cardiac signals.

11. The method of claim 10, further comprising:
generating a timing beacon;
receiving the timing beacon at each active electrode;
wherein the step of generating a cardiac signal includes amplifying a difference between the physiological potentials sensed by the electrode pad and the comparator signal and sampling the amplified difference with an analog-to-digital converter based on the timing beacon.

12. The method of claim 10, further comprising identifying with a processor in a hub device a placement location for each of the two or more active electrodes.

13. The method of claim 12, wherein the step of identifying the placement location includes counting a number of active electrodes transmitting cardiac signals to the hub device and identifying a set of placement locations based on the number of active electrodes.

14. The method of claim 13, further comprising comparing the one or more ECG waveforms to a signal pattern for each placement location and identifying the placement location of the set of placement locations that is most probable for each active electrode based on the comparison.

15. The method of claim 12, wherein the step of identifying the placement location includes receiving user input indicating the placement location for each active electrode.

16. The method of claim 15, wherein receiving the user input includes detecting with an accelerometer in each active electrode a tapping of each active electrode in a predefined order.

17. The method of claim 12, further comprising communicating the placement location of each active electrode to that active electrode and indicating the respective placement location on each active electrode.

18. The method of claim 17, wherein the step of indicating the respective placement location on each active electrode includes displaying an alphanumeric indicator associated with the respective placement location on a digital display on the active electrode or displaying a color indicator associated with the respective placement location with a color LED on the active electrode.

* * * * *